United States Patent [19]

Schütze et al.

[11] Patent Number: 4,461,911
[45] Date of Patent: Jul. 24, 1984

[54] PROCESS FOR THE PREPARATION OF S-ARYLTHIOGLYCOLIC ACIDS

[75] Inventors: Detlef-Ingo Schütze, Bergisch-Gladbach; Anton Adams, Siegburg, both of Fed. Rep. of Germany

[73] Assignee: Bayer Aktiengesellschaft, Leverkusen, Fed. Rep. of Germany

[21] Appl. No.: 382,549

[22] Filed: May 26, 1982

[30] Foreign Application Priority Data

Jun. 11, 1981 [DE] Fed. Rep. of Germany ....... 3123157

[51] Int. Cl.$^3$ .......................................... C07C 149/40
[52] U.S. Cl. ............................... 562/427; 260/465 D; 260/376; 546/153; 546/174; 560/10; 560/18; 562/431
[58] Field of Search ............................ 562/431, 427; 260/465 D, 376; 560/10, 18; 546/153, 174

[56] References Cited

U.S. PATENT DOCUMENTS

2,061,186  11/1936  Cole ...................................... 562/431

FOREIGN PATENT DOCUMENTS

194040  1/1908  Fed. Rep. of Germany .
201231  9/1908  Fed. Rep. of Germany .
274108  9/1970  U.S.S.R. .............................. 562/431

OTHER PUBLICATIONS

Chemical Abstracts, vol. 52, No. 11, Jun. 10, 1958 column 9051.

*Primary Examiner*—Michael L. Shippen
*Attorney, Agent, or Firm*—Sprung, Horn, Kramer & Woods

[57] ABSTRACT

Process for the preparation of S-arylthioglycolic acids of the formula

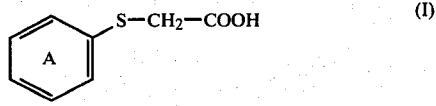
(I)

in which A designates a benzene ring, which can be substituted by 1, 2, 3, 4 or 5 substituents from the series halogen, nitro, hydroxyl, mercapto, trifluoromethyl, alkyl, aryl, alkoxy, aryloxy, acylamino, alkylamino, arylamino, alkylmercapto, arylmercapto, cyano, carboxyl, alkylcarbonyl, arylcarbonyl, alkoxycarbonyl, aryloxycarbonyl or optionally substituted aminocarbonyl, or represents a benzene ring, which optionally carries 1 or 2 of the previously mentioned substituents, to which a carbocyclic or heterocyclic aromatic ring is attached, characterized in that aryldiazonium salts of the formula

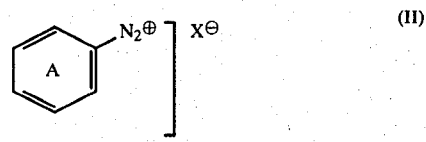
(II)

in which
A has the meanings given for the formula (I) and
X designates the radical of an acid capable of forming a salt with the diazonium cation, are reacted with thioglycolic acid in an aqueous acid medium in the presence of Cu(I) or Cu(II) salts and the reaction mixture is worked up to compounds of the formula (I) or their salts.

18 Claims, No Drawings

PROCESS FOR THE PREPARATION OF S-ARYLTHIOGLYCOLIC ACIDS

BACKGROUND OF THE INVENTION

The invention relates to an improved process for the preparation of S-arylthioglycolic acids by reaction of aromatic diazonium salts with thioglycolic acid in the presence of copper salts, particularly those of divalent copper.

Processes for the preparation of S-arylthioglycolic acids by reaction of aromatic diazonium salts with thioglycolic acid have been known for decades. A process is described as early as German Patent Specification No. 194,040 in which aromatic diazonium salts are allowed to act on thioglycolic acid and the resulting reaction product, the aryldiazomercaptoacetic acid, is converted, directly or after previous isolation, into the S-arylthioglycolic acid by heating, nitrogen being split off.

In another process, described in German Patent Specification No. 201,231, the decomposition of the aryldiazomercaptoacetic acid to the S-arylthioglycolic acids is carried out at temperatures of 20° to 40° C. by addition of copper powder.

Furthermore, the process of German Patent Specification No. 201,232 is known, by which the decomposition to the S-arylthioglycolic acids is carried out by heating in alkaline solution.

In addition, a process for the preparation of 2,3-dichlorophenylthioglycolic acid is described in Swiss Patent Specification No. 451,921, Example 1, in which the reaction of the aromatic diazonium salt with the thioglycolic acid is carried out in alkaline solution at 0° to 5° C.

The disadvantage of all these processes is that yields of only 20 to 50% can be obtained, and the S-arylthioglycolic acids produced are very impure. In addition, an industrial operation in which an aryldiazomercaptoacetic acid, which tends very readily to decompose very violently, arises as an intermediate is very problematical.

SUMMARY OF THE INVENTION

Surprisingly, it has now been found that S-arylthioglycolic acids can be obtained in very good yields and with high degrees of purity when aryldiazonium salts are reacted with thioglycolic acid in the presence of copper salts, in particular copper(II) salts, in an acid medium.

The novel process for the preparation of S-arylthioglycolic acids of the formula

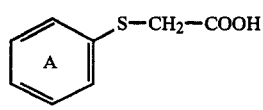

in which A designates a benzene ring, which can be substituted by 1, 2, 3, 4 or 5 substituents from the series halogen, nitro, hydroxyl, mercapto, trifluoromethyl, alkyl, aryl, alkoxy, aryloxy, acylamino, alkylamino, arylamino, alkylmercapto, arylmercapto, cyano, carboxyl, alkylcarbonyl, arylcarbonyl, alkoxycarbonyl, aryloxycarbonyl or optionally substituted aminocarbonyl, or represents a benzene ring, which optionally carries 1 or 2 of the previously mentioned substituents, to which a carbocyclic or heterocyclic aromatic ring is attached, is characterized in that aryldiazonium salts of the formula

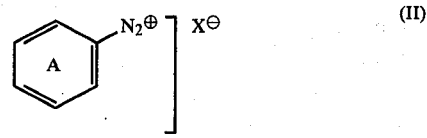

in which

A has the meanings given for the formula (I) and

X designates the radical of an acid capable of forming a salt with the diazonium cation, are reacted with thioglycolic acid in an aqueous acid medium in the presence of Cu(I) or Cu(II) salts, and the reaction mixture is worked up to compounds of the formula (I) or their salts.

Examples of compounds of the formula (I) which may be prepared according to the invention, and which possess an attached carbocyclic or heterocyclic ring, are: α- and β-anthraquinonylthioglycolic acid, α- or β-naphthylthioglycolic acid, quinolinylthioglycolic acid.

In the formula (I) and (II), halogen is preferably chlorine, bromine or fluorine, alkyl is preferably $C_1$–$C_6$-alkyl, aryl is preferably phenyl and naphthyl, alkoxy is preferably $C_1$–$C_6$-alkoxy, acyl is preferably ($C_1$–$C_6$-alkyl)-carbonyl and benzoyl; aminocarbonyl can, for example, be mono- or di-substituted on the N atom by $C_1$–$C_6$-alkyl and/or phenyl.

The process preferably serves to prepare S-arylthioglycolic acids of the formula

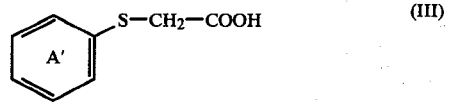

in which A' designates a benzene ring, which can be substituted by 1, 2 or 3 substituents from the series halogen, in particular chlorine, alkyl, in particular methyl and ethyl, alkoxy, in particular methoxy and ethoxy, carboxy, nitro or trifluoromethyl, or to which another benzene ring is fused.

The novel process is of particular interest for the preparation of

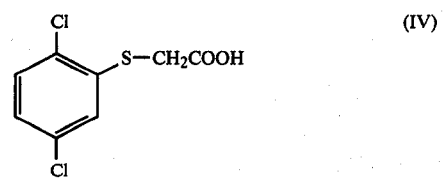

The aryldiazonium salts (II) to be employed as starting compounds for carrying out the process are prepared by procedures known from the literature by diazotization of the corresponding arylamines in an aqueous acid medium, for example with sodium nitrite. This diazonium salt solution is then immediately allowed to run into a mixture consisting of thioglycolic acid and the copper salt in water, the reaction starting immediately with evolution of nitrogen.

The afore-mentioned procedure is much preferred. However, if the diazonium salts are sufficiently stable, these can also be isolated before the subsequent reaction.

In formula (II), $X^\ominus$ preferably represents $Cl^\ominus$.

The amounts and the mixing ratio of the thioglycolic acid and the copper salt in water can be varied in wide ranges depending on the type of S-arylthioglycolic acid to be prepared. For example, 1 to 1.8 mol, preferably 1.2 to 1.5 mol, of thioglycolic acid and 0.1 to 1.2 mol, preferably 0.6 to 1.0 mol, of the copper salt are employed per 1 mol of aryldiazonium salt. The amount of water with the ratios given above is about 0.1 to about 1.5 liters.

Examples of copper salts which can be employed are copper(I) chloride, copper(II) chloride, copper(I) bromide, copper(II) bromide, copper(I) iodide, basic copper(II) carbonate, copper(II) sulphate, copper(II) acetate, copper(II) iodide and the like. Salts of bivalent copper are preferred.

The temperature of reaction is preferably about 0° to about 70° C., particularly preferably about 20° to about 30° C. The pH of the reaction medium is preferably between 0 and 4.5, particularly preferably between 0.5 and 1.5. The reaction times are generally between 15 and 60 minutes, depending on the type of aryldiazonium salt to be reacted. The reaction mixture can be worked up in various ways.

For example, the acid reaction mixture can be heated to 40° to 50° C., and the S-arylthioglycolic acid directly isolated. Another process consists in making the reaction mixture alkaline, the S-arylthioglycolic acid going into solution as a salt and the copper being precipitated. After separating off the copper, the S-arylthioglycolic acid is precipitated by addition of acid and isolated. By this means, the S-arylthioglycolic acids are obtained with a high degree of purity and in very good yields.

The S-arylthioglycolic acids obtainable by the process according to the invention are valuable intermediates, for example for the preparation of vat dyes and pigments.

EXAMPLES

Example 1

(a) Preparation of a solution of 2,5-dichlorophenyldiazonium chloride: 40.5 g of 2,5-dichloroaniline are stirred in 64 ml of 36% strength hydrochloric acid to form the hydrochloride. Then this is diluted with 300 ml of water and 450 g of ice, and diazotized by addition of a solution of 18 g of sodium nitrite in 60 ml of water. After the mixture has been stirred for 1 hour, the excess nitrite is destroyed with a solution of 1.6 g of amidosulphonic acid in 17 ml of water. This solution is then reacted.

(b) Thioglycolic acid reaction: 29.9 g of thioglycolic acid and 16.6 g of basic copper carbonate are stirred in 250 ml of water for 30 minutes. The diazonium salt solution prepared according to (a) is then allowed to run in at 20°–25° C. in 15 minutes. The reaction starts immediately with evolution of nitrogen. After a further 30 minutes stirring, 55 ml of 50% strength sodium hydroxide solution are added (pH 7–7.5), and the mixture is heated to 70° C. and stirred for 1 hour. Thereafter a further 20 ml of 50% strength sodium hydroxide solution are added (pH 7.5–8), and the mixture is heated to 95°–100° C., stirred for 30 minutes and filtered hot to remove the copper hydroxide. Then the filtrate is stirred in 85 ml of 36% strength hydrochloric acid, and the precipitated 2,5-dichlorophenylthioglycolic acid is filtered off with suction, washed with a little water and dried. 48.1 g of 2,5-dichlorophenylthioglycolic acid are obtained, which is 80.3% of theory. The acid obtained is 98.8% pure, and the melting point is 129°–130° C.

Example 2

32.2 g of thioglycolic acid and 56.4 g of crystalline copper sulphate are stirred for 30 minutes in 250 ml of water. Then a solution of 2,5-dichlorophenyldiazonium chloride prepared according to Example 1(a) is allowed to run in at 20° C. in 15 minutes. After a further 30 minutes' stirring, 64 ml of 36% strength hydrochloric acid are added and the mixture is stirred one hour at 40°–50° C. It is then filtered hot with suction and washed with 5% strength hydrochloric acid.

The moist filtered solid is again stirred in 800 ml of water, brought to solution with 30 g of sodium carbonate, and heated to boiling for 15 minutes with 7.5 g of active charcoal to clarify. It is filtered hot, and the filtrate is added to 85 ml of 36% strength hydrochloric acid to precipitate out the 2,5-dichlorophenylthioglycolic acid. This is filtered off with suction, washed with a little water and dried.

49.8 g of 2,5-dichlorophenylthioglycolic acid are obtained, which is 83.9% of theory. The acid is 99.8% pure and has a melting point of 129°–130° C.

Example 3

A mixture analogous to Example 2, but employing 29.7 g of copper(I) chloride instead of 56.4 g of copper sulphate, is stirred.

44.9 g of 2,5-dichlorophenylthioglycolic acid are obtained, which is 74.6% of theory. The acid obtained is 98.5% pure with a melting point of 129°–130° C.

EXAMPLE 4

32.2 g of thioglycolic acid and 56.4 g of crystalline copper sulphate are stirred for 30 minutes in 250 ml of water. Then an aqueous solution of 3-ethoxyphenyldiazonium chloride, prepared according to Example 1(a) from 34.3 g of 3-ethoxyaniline, is allowed to run in at 25° C. in 20 minutes. After a further 40 minutes' stirring, 64 ml of 36% strength hydrochloric acid are added. The mixture is stirred for 1 hour at 40°–50° C., filtered hot with suction and washed with 5% strength hydrochloric acid. The moist filtered solid is dissolved in 500 ml of water with 30 g of sodium carbonate, and heated to boiling with 5 g of active charcoal for 15 minutes. It is filtered hot and the filtrate is added to 85 ml of 36% strength hydrochloric acid to precipitate the 3-ethoxyphenylthioglycolic acid. It is filtered off with suction, washed with a little water and dried. 40.4 g of 3-ethoxyphenylthioglycolic acid are obtained, which is 75.7% of theory. The acid is 99.5% pure with a melting point of 105°–107° C.

Examples 5 to 20

If the process is carried out analogously to Examples 1 to 4, but using the aromatic amines listed in the table below, or their corresponding diazonium salt solutions, the listed arylthioglycolic acids are obtained as a rule in the same purity and in yields of 75% to 85% of theory.

| Example No. | Arylamine | Arylthioglycolic acid |
|---|---|---|
| 5 | aniline (NH₂-C₆H₅) | Phenylthioglycolic acid |
| 6 | 4-methylaniline | 4-Methylphenyl-thioglycolic acid |
| 7 | 2-chloroaniline | 2-Chlorophenyl-thioglycolic acid |
| 8 | 2,4-dichloroaniline | 2,4-Dichlorophenyl-thioglycolic acid |
| 9 | 2-methyl-5-chloroaniline | 2-Methyl-5-chlorophenyl-thioglycolic acid |
| 10 | 2-methyl-4-chloroaniline | 2-Methyl-4-chlorophenyl-thioglycolic acid |
| 11 | 2,5-dimethyl-4-chloroaniline | 2,5-Dimethyl-4-chlorophenyl-thioglycolic acid |
| 12 | 3-methyl-5-chloroaniline | 3-Methyl-5-chlorophenyl-thioglycolic acid |
| 13 | 2,5-dichloro-3-methylaniline | 2,5-Dichloro-3-methylphenyl-thioglycolic acid |
| 14 | 4-methoxyaniline | 4-Methoxyphenyl-thioglycolic acid |
| 15 | 4-nitroaniline | 4-Nitrophenylthioglycolic acid |
| 16 | 3-trifluoromethylaniline | 3-Trifluoromethylphenyl-thioglycolic acid |
| 17 | 2-methoxy-5-chloroaniline | 2-Methoxy-5-chlorophenyl-thioglycolic acid |
| 18 | 2-methoxy-5-methylaniline | 2-Methoxy-5-methylphenyl-thioglycolic acid |
| 19 | 2-aminobenzoic acid | 2-Carboxyphenyl-thioglycolic acid |
| 20 | β-naphthylamine | β-Naphthylthioglycolic acid |

We claim:
1. Process for the preparation of S-arylthioglycolic acids of the formula

$$\text{A}\!-\!\text{S}\!-\!\text{CH}_2\!-\!\text{COOH} \qquad (I)$$

in which
A designates a benzene ring, which can be substituted by 1, 2, 3, 4 or 5 substituents selected from the group consisting of halogen, nitro, hydroxyl, mercapto, trifluoromethyl, alkyl, aryl, alkoxy, aryloxy, acylamino, alkylamino, arylamino, alkylmercapto, arylmercapto, cyano, carboxyl, alkylcarbonyl, arylcarbonyl, alkoxycarbonyl, aryloxycarbonyl, unsubstituted aminocarbonyl and aminocarbonyl which is mono- or di-substituted on the N-atom by $C_1$-$C_6$-alkyl or phenyl, or A represents an unsubstituted benzene ring or a substituted benzene ring, which carries 1 or 2 of the previously mentioned substituents, to which a carbocyclic or heterocyclic aromatic ring is fused to A, wherein aryldiazonium salts of the formula

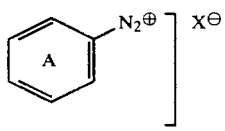

in which

A has the meanings given for the formula (I) and

X designates the radical of an acid capable of forming a salt with the diazonium cation, are reacted with thioglycolic acid in an aqueous acid medium in the present of Cu(I) or Cu(II) salts, and the reaction is allowed to proceed such that the reaction mixture forms compounds of the formula (I).

2. Process according to claim 1 for the preparation of S-arylthioglycolic acids of the formula

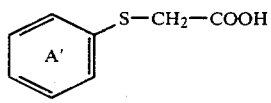

in which

A' designates as a benzene ring, which can be substituted by 1, 2 or 3 substituents selected from the group consisting of halogen, alkyl, alkoxy, carboxyl, nitro and trifluoromethyl, or A' designates a benzene ring to which another benzene ring is fused.

3. Process according to claim 1 for the preparation of

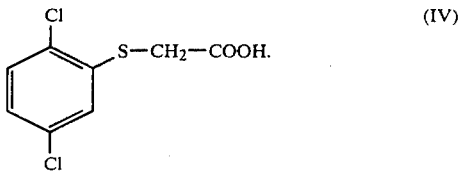

4. Process according to claim 1, wherein copper (II) salts are employed.

5. Process according to claim 1, wherein copper (II) chloride, copper (II) bromide, copper(II) iodide, copper(II) sulphate, copper(II) acetate or basic copper(II) carbonate is employed.

6. Process according to claim 1, wherein the reaction is carried out at a pH between 0 and 4.5.

7. Process according to claim 1, wherein the reaction is carried out at a temperature of about 0° to about 70° C.

8. Process according to claim 1, wherein 1 to 1.8 mol of thioglycolic acid are employed per mol of aryldiazonium salt.

9. Process according to claim 1, wherein 0.1 to 1.2 mol of copper salt are employed per mol of aryldiazonium salt.

10. Process according to claim 1, wherein the reaction mixture containing the synthesized acid is made alkaline, whereby to convert said S-arylthioglycolic acid to the corresponding salt which becomes dissolved in said solution and the copper is precipitated.

11. Process according to claim 10, wherein the copper precipitate is separated off and the S-arylthioglycolic moiety is precipitated by addition of acid and isolated.

12. Process according to claim 1, wherein the reaction is carried out at a pH between 0.5 and 1.5.

13. Process according to claim 1, wherein the reaction is carried out at a temperature of about 20° C. to about 30° C.

14. Process according to claim 1, wherein 1.2 to 1.5 mol of thioglycolic acid are employed per mol of aryldiazonium salt.

15. Process according to claim 1, wherein 0.6 to 1 mol of copper salt are employed per mol of aryldiazonium salt.

16. Process according to claim 2, wherein said halogen is chlorine.

17. Process according to claim 2, wherein said alkyl is selected from the group consisting of methyl and ethyl.

18. Process according to claim 2, wherein said alkoxy is selected from the group consisting of methoxy and ethoxy.

* * * * *